(12) United States Patent
Miltenyi et al.

(10) Patent No.: US 10,273,504 B2
(45) Date of Patent: Apr. 30, 2019

(54) METHOD AND DEVICE FOR CELL MODIFICATION

(71) Applicant: Miltenyi Biotec GmbH, Bergisch Gladbach (DE)

(72) Inventors: Stefan Miltenyi, Bergish Gladbach (DE); Alexander Scheffold, Cologne (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 79 days.

(21) Appl. No.: 15/486,362

(22) Filed: Apr. 13, 2017

(65) Prior Publication Data

US 2017/0218331 A1  Aug. 3, 2017

Related U.S. Application Data

(63) Continuation-in-part of application No. 14/351,889, filed as application No. PCT/EP2012/072431 on Nov. 13, 2012, now abandoned.

(30) Foreign Application Priority Data

Nov. 18, 2011  (EP) ..................... 11189754

(51) Int. Cl.
| | |
|---|---|
| *C12M 1/00* | (2006.01) |
| *C12M 1/42* | (2006.01) |
| *C12N 5/00* | (2006.01) |
| *C12N 15/00* | (2006.01) |
| *C12N 15/87* | (2006.01) |
| *C12N 5/0783* | (2010.01) |

(52) U.S. Cl.
CPC ............ *C12N 15/87* (2013.01); *C12M 35/04* (2013.01); *C12M 35/08* (2013.01); *C12N 5/0636* (2013.01); *C12N 2510/00* (2013.01); *C12N 2525/00* (2013.01)

(58) Field of Classification Search
CPC ...... C12M 35/04; C12M 27/10; C12M 23/20; C12N 15/85
See application file for complete search history.

(56) References Cited

U.S. PATENT DOCUMENTS

| | | |
|---|---|---|
| 6,977,138 B2 | 12/2005 | Lahann et al. |
| 2008/0255004 A1 | 10/2008 | Neurauter et al. |

FOREIGN PATENT DOCUMENTS

| | | |
|---|---|---|
| WO | WO2008/037458 | 3/2008 |
| WO | WO 2009/072003 A2 * | 6/2009 |
| WO | WO2009/072003 | 11/2009 |

OTHER PUBLICATIONS

Galimberti et al. "Hypergravity speeds up the development of T-lymphocyte motility" Eur Biophys J. May 1, 2006 35(5):393-400.
Morbidelli et al. Microgravity Sci technol (2009) 21:135-140.
Versari et al.,"Effects of gravity on proliferation and differentiation of adipose tissue-derives stem cells," J Gravit Physiol, 14(1):p. 127-128 (2007).
Tonks et al., Biotechnol Prog. 2005; (21(3): 953-8.

* cited by examiner

*Primary Examiner* — Janet L Epps-Smith
(74) *Attorney, Agent, or Firm* — Jacquelin K. Spong

(57) ABSTRACT

The invention relates to a cell modification device, comprising a centrifugation chamber with at least one cell modifying surface with a normal vector having an angle of 135–45° to the rotational axis of the centrifugation chamber, wherein the centrifugation chamber comprises at least one input/output port and the cells to be modified are immobilized at the cell modifying surfaces by the rotation of the centrifugation chamber at 2 to 2000 g.

Furthermore, the invention relates to a method for modifying cells comprising the steps
- introducing cells in a cell modification device, comprising a centrifugation chamber with at least one cell modifying surface with a normal vector having an angle of 135–45° to the rotational axis of the centrifugation chamber wherein and comprising at least one input/output port,
- immobilizing the cells on the cell modifying surfaces by the rotation of the centrifugation chamber at 2 to 2000 g
- maintaining the rotation of the rotation of the centrifugation chamber until the cells are modified.

11 Claims, 10 Drawing Sheets

METHOD AND DEVICE FOR CELL MODIFICATION

CROSS REFERENCE TO RELATED APPLICATIONS

This US Patent Application is a Continuation-in-Part from U.S. patent application Ser. No. 14/351,889 filed Apr. 15, 2014, which is a 371(c)(1) application from PCT/EP2012/072431 filed Nov. 13, 2012 which claims priority to European Application EP 11189754.2 filed Nov. 18, 2011.

STATEMENT REGARDING FEDERALLY SPONSORED RESEARCH

Not applicable.

STATEMENT REGARDING MICROFICHE APPENDIX

Not applicable.

BACKGROUND OF THE INVENTION

The present invention relates to methods and devices for modifying eukaryotic cells on functionalized surfaces of a centrifugation apparatus The conditions during cell culturing have a substantial impact on the phenotypes of the cells and desired or not, cell culturing leads to the manipulation of cells.

Cell culture refers to methods under which eukaryotic cells, especially of mammalian origin, are maintained at appropriate conditions with supply of cell culture medium in a cell incubator or a fermenter. Cell culture conditions vary widely depending on the cell type and the desired application. Variation of cell culture conditions can be utilized for cell expansion, cell differentiation or manufacturing of different phenotypes of the cell type. The most commonly varied factor in culture systems is the cell culture medium, for which a vast number of recipes is known (see for example "Cell Culture Techniques" Humana Press, 1st. Edition, 2011).

Typically culture systems utilize a large amount of medium compared to the mass of the cells to provide a sufficient reservoir for nutrients. In static systems, the medium covering the cells is limiting the gas diffusion to the cells if the cell culture surface itself does not allow gas diffusion. Slow macroscopic convection of the medium results in uncontrolled and uneven supply of nutrients to the cells and may result in different differentiated i.e. manipulated cells.

Culturing large numbers of cells adhered to a surface without the use of carriers or large volume cell suspension is difficult and requires frequent change of the medium. The known static systems for cell culturing are labor-intensive and need clean room conditions during handling the cell cultures, for example media exchange or transfer cells from and into storing devices or adequate incubators for proper cell growth. In dynamic systems for cell culturing like roller fermenters, cells can dislocate from the surface of the fermenter and are suspended in the media. The conditions for growing and supply of nutrients is not uniform for adhered and suspended cells and will result in different differentiated or modified cells. Centrifugation systems for the separation or modification of cells are known.

It is long known to separate cells from a cell mixture into fractions of different cell types with the aid of centrifugal forces in a centrifuge according to their density i.e. their sedimentation velocity. The cell separation is carried out in a specially designed centrifuge, rotor and container (flask) for the cells. For example, whole blood is fractionated or separated by centrifugation into blood plasma (as upper phase), buffy coat (thin layer of leukocytes mixed with platelets in the middle phase), and erythrocytes as lower phase.

The effect of enhanced gravity generated by centrifugation on cells under culturing conditions has been investigated in various publications. Huang et al (2009) disclose in "Gravity, a regulation factor in the differentiation of rat bone marrow mesenchymal stem cells" in J. Biomed. Here, rBM-SCs are first plated on glass coverslips; after 24 h the cells had adhered to the coverslips and the coverslips were transferred to a biocompatible polyethylene culture bag, are incubated with medium and then cultured on a cell centrifuge at 2 g hypergravity for several days. The medium was changed every 3 days during HG/SMG culture.

Gaubin et al. described in Microgravity Sci. Technol. 1991 February; 3(4):246-50 the effects of hypergravity on adherent human cells. Galimberti et al disclose in "Hypergravity speeds up the development of T-lymphocyte motility", Eur Biophys J, May 1, 2006; 35(5): 393-400 a hypergravity cell culture for 1 to 11 days. Cell culture is performed in flasks which were positioned vertically to the centrifugation axis in the centrifuge. The use of flasks within a centrifuge is furthermore proposed by Versati et al in "Effects of gravity on proliferation and differentiation of adipose tissue-derived stem cells", J Gravit Physiol, 14(1): P127-128 (2007). Here, a commercial available medium sized centrifuge (MidiCAR) is used to accommodate cell culture flasks to investigate cell growth under hypergravity conditions. Morbidelli et al. investigated in Microgravity Sci. technol (2009) 21:135-140 the effect of hypergravity on endothelial cell function and gene expression. Cell manipulation or cell modification is not disclosed in this publication.

The methods disclosed in these publications are with the exception of hypergravity conditions nearly identical to common cell culturing and involve manual handling steps like medium change. Change of medium i.e. the supply of cells to be cultured with nutrients involves stopping of the centrifugation process, thereby interruption of the enhanced gravitational forces. Manual handling steps are not only laborious and prone to contamination, but also destroy the micro environment of the cells like cell/cell contact or cell/cell interaction. An unaffected micro environment of the cells is important for cell cultivation, e.g. for the activation of lymphocytes or viral or retroviral transduction processes. There is no disclosure in the prior art about the nature of the surface of the flasks or the centrifugation chamber.

It is further known that retroviral transduction of cells can be accelerated by hypergravity, for example described by Tonks et al in Biotechnol Prog. 2005; 21(3): 953-8. With this technique, retrovirus vectors are coated on plates and cells are brought into contact with the virus. In order to promote the contact between target cells and the virus vector, the plate comprising adhered virus and cells are placed into a centrifuge. This requires manual handling steps and the cells are not supplied with medium during centrifugation.

WO 2009/072003 discloses a centrifugation system for cell proliferation. Cell manipulation or cell modification is not disclosed in this publication.

The invention provides a novel device and method for modifying cell populations on functionalized cell modifying surfaces under hypergravity conditions generated by the rotation of a centrifugation chamber. With the device and method of the invention, eukaryotic cells can be modified and/or eukaryotic cells with new or modified features can be generated.

SUMMARY OF THE INVENTION

It is a first object of the invention to provide a cell modification device, comprising a centrifugation chamber with at least one cell modifying surface with a normal vector having an angle of 135–45° to the rotational axis of the centrifugation chamber, wherein the centrifugation chamber comprises at least one input/output port and the cells to be modified are immobilized at the cell modifying surfaces by the rotation of the centrifugation chamber at 2 to 2000 g.

The device of the invention comprises a centrifugation chamber with at least one input/output port through which cells, cell culturing liquids (media), gases and other materials can enter and leave the chamber without the need of stopping the rotation of the centrifugation chamber. The device comprises preferable one input port and one output port for liquids and at least one, especially two for gases.

Another object of the invention is a method for modifying cells comprising the steps
  introducing cells in a cell modification device, comprising a centrifugation chamber with at least one cell modifying surface with a normal vector having an angle of 135–45° to the rotational axis of the centrifugation chamber wherein and comprising at least one input/output port,
  immobilizing the cells on the cell modifying surfaces by the rotation of the centrifugation chamber at 2 to 2000 g
  maintaining the rotation of the rotation of the centrifugation chamber until the cells are modified.

Cell modification according to the invention relates to all methods where cells are kept physiologically active and are modified. The modification may result for example in a change of the phenotype, function, number or differentiation status of the cells, like
a) cell division, differentiation or cell proliferation
b) activation of a signal transduction cascade
c) change of the cellular activation status and/or cell function
d) genetic modification of cells
e) growing of layers of different or identical cell types involving cell-cell contact The modification of the cells results for example in a change of expression of certain proteins, of RNA molecules, of miRNA, in a change of post translational modification, in a change of DNA methylation or in histone modification.

The cell modification device comprises cell modifying surfaces which can be functionalized for cell modification.

The mechanical/chemical stimulus changing the phenotypes of the cells is provided or triggered by the functionalized cell modifying surfaces of the centrifugation chamber of the invention. The term "functionalized surface" as used in this application includes all types of surfaces which can provide a stimulus to a cell. Typically, functionalized cell modifying surface comprise a coating of chemical or physical immobilized bioactive compounds, like
  proteins, peptides, nucleic acids;
  spacer molecules enhancing the adhesion of cells or bioactive compounds to the cell modifying surfaces like hydrophilic polymers (functionalized poly lactate, polyvinyl alcohols, polysaccharides; functionalized dextranes);
  organic or inorganic particles as carrier of bioactive compounds, especially magnetic particles coated with functionalized poly lactate, polyvinyl alcohols or functionalized dextranes;
  substances enhancing cell adhesion, e.g polypeptides, lipids, polysaccharides;
  viruses and retroviruses or particles thereof
  cells which can be used for modification of a target cell, such as antigen presenting cells, "accessory cells" producing certain bioactive factors or cell lines transfected with certain functional molecules.
  stimulus provided by mitogens, cytokines, stimulatory antibodies or receptor ligands The cell modification device according to the invention comprises at least one cell modifying surface which is functionalized for example for adherence, proliferation, genetic and/or cellular modification of the cells, or for proliferation of cells in one or more layers.

The cell modification device according to the invention comprises preferable at least one cell modifying surface which is functionalized with at least one substance enhancing proliferation of cells, and/or inducing genetic modification and/or inducing cellular modification of cells. The cell modifying surface can further be functionalized with particles being functionalized with at least one substance enhancing proliferation of cells, and/or inducing genetic modification and/or inducing cellular modification of cells.

Surface Functionalization with Cell Binding Systems

In a first embodiment of the invention, the cell modifying surfaces may be functionalized with any substance which is suitable for cell culture and useful or required to introduce preferable cell culture conditions for a given cell type.

The cell modifying surfaces can be functionalized in order to enhance adherence and/or proliferation of cells on the cell modifying surfaces. Suitable substances for functionalization of the surfaces are glycoproteins, polypeptides, glycosaminoglycans, disaccharides, biotin binding molecules or protein tags. For example, the surface may be coated with extracellular matrix proteins including all collagen types (I to VIII).

Furthermore, the cell modifying surfaces may comprise an affinity binding system. One of the most widely used affinity binding system is the avidin-biotin or streptavidin-biotin system. For example, the cell modifying surface may be first coated with avidin and/or streptavidin (or derivates thereof) to facilitate binding of a biotinylated molecule like a biotinylated antibody. It is furthermore possible to coat the cell modifying surface first with biotin (or derivates thereof) to facilitate binding of another molecule functionalized with streptavidin and/or avidin. Both variants result in high affinity binding of the second molecule to the cell modifying surfaces. The strong interaction between streptavidin or avidin-biotin is made much weaker by using a combination of modified streptavidin or avidin and modified biotin like desthiobiotin or a derivative thereof like DSB-X Biotin (Hirsch et al. 2002: "Easily reversible desthiobiotin binding to streptavidin, avidin, and other biotin-binding proteins: uses for protein labeling, detection, and isolation". Analytical Biochemistry 308: 343-357; US2008/0255004A1). A protein, such as an antibody may be biotinylated with the modified biotin. When this protein is immobilized by binding the modified biotin to an optionally modified streptavidin or avidin molecule bound to the cell modifying surface, it may be released under mild conditions by adding free biotin.

The functionalizing of the cell modifying surface like coating with biotin or (strept)avidin may be performed before or during the process of the invention, both inside or outside of the centrifugation chamber or the device of the invention. The renewal of the coating or the functionalization of the cell modifying surface may be performed between two process steps and without interruption of the rotation of the centrifugation chamber. For example, the renewal of the functionalized cell modifying surface is possible by adding biotinylated molecules or molecules with (strept)avidin to a cell modifying surface which is coated with streptavidin or biotin, respectively.

Further affinity binding systems suitable for the cell modifying surfaces comprise antibodies, for example antibodies against biotin or protein tags for example IIsopeptago, BCCP or Myc-tag.

The cell modifying surfaces may be further be coated with libraries of substances synthesized with methods of combinatorial chemistry in order to identify substances which work best as binding system for a given cell type.

Certain bioactive polymers may be used as spacer molecules enhancing the adhesion of cells or the binding of other substances on the cell modifying surfaces like functionalized poly lactic acid, polyvinyl alcohols, polysaccharides or dextranes or derivates thereof. This binding system is especially useful as basic coating of a cell modifying surface produced from a hydrophobic plastic material like poly carbonate, polystyrene or polyethylene. The cell modifying surfaces may be coated with highly reactive polymers as e.g. disclosed in U.S. Pat. No. 6,977,138B2.

The cell modifying surfaces can comprise one or more substances which enhance adhesion and/or proliferation of cells. Especially useful are one or more substances selected from the group consisting of collagen types (I to VIII), fibronectin, gelatin, laminin, elastin, hyaluronic acid, keratan sulfate, chondroitin sulfate, heparan sulfate proteoglycans, poly-d-lysine, avidin, streptavidin, biotin, antibodies, antibodies against biotin or protein tags, protein tags like IIsopeptag, BCCP, Myc-tag, Calmodulin-tag, FLAG-tag, HA-tag, His-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty tag, certia, poly lactate, polyvinyl alcohols, polysaccharides and dextran.

Surface Functionalization for Cellular Modification

In a second embodiment of the method of invention, cell modification comprises cellular modification like activation, proliferation, dedifferentiation and/or differentiation of cells. Accordingly, the cell modifying surfaces may be functionalized with any substance which is suitable for cellular modification of cells like cell activation, proliferation, dedifferentiation and differentiation of cells. The cell modifying surface can further be functionalized with particles being functionalized with at least one substance suitable for cellular modification of cells like cell activation, proliferation, dedifferentiation and differentiation of cells.

Particular, cell modification by the method and the device of the invention comprises the alteration of gene expression, protein expression, post-translational or posttranscriptional modifications of genes, mRNAs or proteins, protein phosphorylation, histone modification, or modification of intracellular signaling cascades (e.g. Ca2+ influx).

Furthermore, cellular modification may comprise cell activation for example by agonistic or antagonistic antibodies, cytokines, growth factors, (de-)activating ligands, pharmacologically active substances, mitogens, DNA or RNA-modifying substances.

The cell modifying surfaces can be functionalized for one or more cellular modification steps.

Surface Functionalization for Genetic Modification

In a third embodiment of the invention, the cell modifying surfaces may be functionalized with any substance which is suitable for genetic modification of cells, i.e. modification of cells using genetic material or any other substances interacting, binding or integrating into cellular polynucleotides or the genome and/or altering their function. Again, the cell modifying surface can further be functionalized with particles being functionalized with at least one substance suitable for genetic modification of cells, i.e. modification of cells using genetic material or any other substances interacting, binding or integrating into cellular polynucleotides or the genome and/or altering their function.

Genetic modification of a cell according to this invention includes for example transduction by viral, such as adenoviral or retroviral or lentiviral vectors or transfection with nucleic acids, i.e. coding RNAs, non-coding small or large RNAs (i.e. siRNA, miRNA, shRNA), DNA, mRNA- or shRNA-expression plasmids or other substances interacting or binding or integrating into cellular polynucleotides or the genome and/or altering their function.

Genetic modification furthermore comprises contacting the cells for example with a virus, viral particle, RNA, DNA, protein, ligand, receptor, cytokine, stimulating or deactivating antibody, pharmacological agent, other cells (e.g. feeder cells) or layers of several cells or cell types. The contacting agent can be soluble in the cell culturing liquid or attached to the cell modifying surfaces, or can be expressed or anchored to the surface of another cell used for co-culture.

The cell modifying surfaces can be functionalized for one or more genetic modification steps.

Surface Functionalization for Cell Layers

Culturing cells on flat cell modifying surfaces often results in two-dimensional sheets, which is an artificial environment for any cell. Eukaryotic cells experience in vivo a three-dimensional environment and are surrounded by other cells, membranes, fibrous layers and adhesion proteins. Three-dimensional cell cultures are known and use as support extracellular matrices, scaffolds and proteins to provide an in vivo-like morphology and physiologically relevant environment. Commercially available 3D cell culture systems are e.g. MaxGel™ human Extracellular Matrix (ECM), HydroMatrix™ synthetic peptide, and mouse ECM, from Sigma® to support stem cell and other cell cultures.

A forth object of the invention is to provide a layered cell composition, wherein cells are grown in a layered system like tissue or organs. For this purpose, the device and the method of the invention is used to immobilize cells at defined positions, e.g. in successive layers of same or different cell types, and to keep the cells at a fixed position by the centrifugal forces, allowing building of complex layers. In addition to be grown in a layered system, the cells may further be modified as described above.

The cell modifying surfaces of the device of the invention can comprise one or a plurality of identical or different functionalized cell modifying surfaces. For example, the cell modifying surfaces can be equipped with an affinity binding system in addition to functionalization of the surface for genetic modification of the cells.

DETAILED DESCRIPTION OF THE INVENTION

Figure 1:
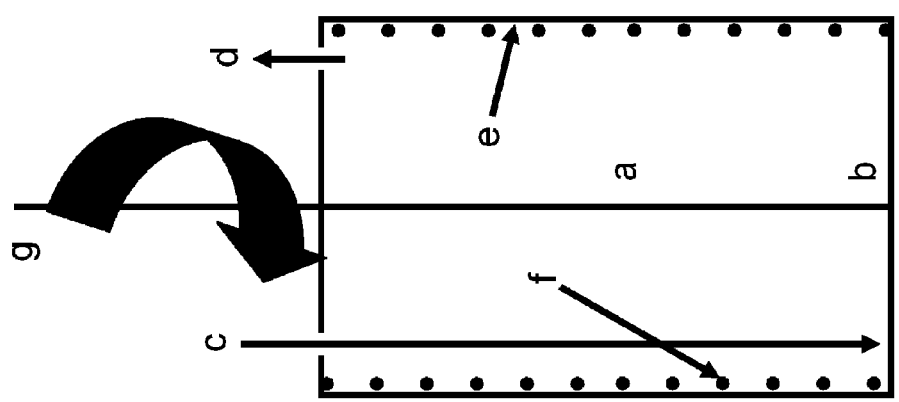
FIG. 1 is a schematic view of a cell modification device used in embodiments of the invention.

In general, cell modification of the invention involves cell culturing conditions where cells are kept physiological active over a period of time. This is usually accomplished at temperatures of 25-45° C. and with a supply of nutrients like glucose and gases like $O_2$ and $CO_2$. During the culturing process, the conditions can be maintained stable or are subject to changes such as hyper/hypoxia conditions, in-/decreased pressure, different gravitational forces, in-/decreased supply of nutrients or growth factors, in-/decreased temperature, high or low cell density, in-/decreased medium osmolarity, or gradients of nutrients, chemokines/cytokines/growth factors or stimulatory/deactivating antibodies.

Cell Media

In the method of the invention, various cell culturing liquid (media) known in the art of cell culturing can be used as stimulus for cells, including one or more of the following media DMEM, HBSS, DPBS, RPMI, Iscove's medium, X-VIVO™, each optionally supplemented e.g. with fetal calf serum, human serum or serum substitutes or other nutrients or cell stimuli like Cytokines. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cell expansion). The media may have supplements or reagents well known in the art, e.g. albumins and transport proteins, amino acids and vitamins, antibiotics, attachments factors, growth factors and cytokines, hormones or solubilising agents. Various media are commercially available e. g. from LifeTechnologies or Sigma-Aldrich.

Centrifugation Conditions

During cell modification in the device and the method of the invention, the cells to be modified are immobilized at the cell modifying surfaces by the gravitational forces due to the rotation of the centrifugation chamber.

The invention is preferably carried out at a rotational speed of the centrifugation chamber generating centrifugal forces of more than 1 g and up to 2000 g, preferable between 20 and 1000 g, more preferable between 20 and 500 g and especially preferable between 20 and 100 g.

The degree of cell modification can be adjusted by the speed of rotation of the centrifugation chamber, since the gravitational forces enacting on the cells depend on the speed of the centrifugation chamber, density of the culturing media, density of the cells and the distance of an individual cell to the rotational axis of the centrifugation chamber.

The magnitude of centrifugal forces F acting on a given cell depends on the mass m of the cell, its speed, i.e. its angular velocity to, and the radius r of curvature, i.e. the distance between the cell and the rotational axis of the chamber, according to the following formula $$F=mr\omega^2$$

The mass m of the cell is calculated from the cell volume ($V_{cell}$) and the cell density ($\delta_{cell}$). Cell density $\delta_{cell}$ of eukaryotic cells is between 1.04 and 1.09 g/cm$^3$. Taking into account the buoyant force relative to the media density ($\delta_{media}$), the centrifugal force F can be calculated as follows $$F=(\delta_{cell}-\delta_{media})V_{cell}r\omega^2$$

The angular velocity can be expressed as rotations of the chamber per time ($2\pi/T$). If a individual cell is located at the inner wall of the chamber, r equals the inner radius of the chamber.

The degree of interaction between surface and cell may be modified changing the density of the medium. Typically, media density ($\delta_{media}$) is around 1.0 g/cm$^3$, but can be changed by appropriated additives. Accordingly, cells can be released during the process of the invention from the cell modifying surfaces by utilizing a cell medium with a higher density or enhancing the density of the cell medium by adding appropriated additives.

The cell modification according to the invention involves centrifugation conditions applied to the cells as long as necessary to induce the desired modification of the cells. The duration of the centrifugal forces depends on the desired modification of the cells and is not limited. Centrifugal forces may be applied to the cells during the process of the invention for as short as 10 s or as long as 10 days. Typically, centrifugal forces of more than 2 g, especially more than 5 g or more than 10 g are applied for at least 40, 120 or 360 minutes up to 720 minutes.

It is also possible to maintain centrifugation at the same speed during the entire process or to use a sequence of several (2-50) periods of centrifugal forces with same or different speed of rotation. The duration of the centrifugal forces may vary, depending on the desired modification of the cells. For example, the speed of rotation may be higher if a process step for genetic and/or cellular modifications of cells is involved compared to rotational speed during steps for culturing and/or expanding the cells. The continuous flow of liquid through the centrifugation chamber and/or over the cell modifying surfaces can be achieved through variation of the centrifugal forces i.e. through a variation of speeds of rotation of the chamber.

Use of Particles

Modification of cells with the device and method of the invention may further comprise the use of particles, especially particles having functionalized (i.e. biologically active) surfaces. The particles may be produced from organic material like polymers (poly dextranes, poly saccharides, poly styrene, poly lactides or polyvinyl alcohol, each chemically modified or unmodified) or inorganic material like silica, alumina or ferromagnetic metals or metal oxides. Particles made from inorganic material may be coated with the polymers mentioned. The size of the particles depends on their intended function and may vary between 20 nm and 500 µm.

Preferable, the particles are coated or at least doped with biologically active substances. The biologically active substances may be mixed with the bulk material of the particle and can be released during the process of the invention. In another variant, the biologically active substances are only present on the outer surface of the particles.

The particles may contain or be coated with all biologically active substances already disclosed in the present application for surface functionalization for cell layers, surface functionalization with cell binding systems, surface functionalization for cellular modification or surface functionalization for genetic modification.

Particles may be coated or immobilized by the centrifugal forces on the cell modifying surfaces before introducing the cells to be modified into the centrifugation chamber. In this case, the cells are immobilized by the centrifugal forces on the particles. In another variant or the method of the invention, first the cells to be modified are immobilized by the centrifugal forces on the cell modifying surfaces. Then, the particles are introduced into the centrifugation chamber, for example as suspension in the cell media. In this variant of the invention, the particles are immobilized by the centrifugal forces on the cells.

The particles and/or biologically active substances are brought into close contact with the cells to be modified with the aid of the centrifugal forces exerted on the cell membrane of the cells. Depending on the centrifugal forces exerted on the cell membrane of the cells, it is even possible that the particles and/or biologically active substances are introduced into the cells. Substances which transiently permeabilize the cell membrane can be added to assist this process.

Particles can be used in any process step of the invention, alone or in addition to other disclosed biologically active substances or coatings.

Sequence of Processing Steps

In another embodiment of the method of the invention, the cells are subjected to a sequence of at least two different gravitational forces i.e. rotational speeds of the centrifugation chamber. In this embodiment, at least two different process steps can be performed, each with a rotational speed adapted for the respective process step.

A sequence of same or different centrifugal forces applied on the cells (i.e. rotational speed of the centrifugation chamber) allows the control of the kind or the degree of cell modification. For example, the cells can be genetically modified by transducing with virus particles in a first processing step at a rotational speed generating centrifugal forces of 100 g to 1000 g and thereafter cultured/expanded in a second processing step at a rotational speed generating centrifugal forces of 2 g to 100 g.

The method of the invention can comprise a sequence of processing steps consisting of at least two centrifugation steps with the same or different centrifugal forces applied which are optionally interrupted by for example the change or renewal of the cell modifying surfaces or culturing media, or the addition of stimulating substances or cells. The exchange or renewal of any material can be performed during the process of the invention without opening the centrifugation chamber.

For example, the method of the invention can comprise a sequence of processing steps, wherein cells are first introduced into the chamber and immobilized at the functionalized cultural surfaces by the rotation of the centrifugation chamber. After a first modification, like a proliferation step, the cells are rinsed at low rotational speed of the chamber from the cell modifying surfaces into a buffer container via the inlet/outlet port. Then, the centrifugation chamber may be stopped and a new (same or different) coating may be applied to the cell modifying surfaces. In an alternative variant of the invention, the rotation of the chamber is not stopped, and the cell modifying surfaces are coated with the same (fresh) or a different functionalized coating under ongoing rotation of the chamber. An affinity binding system as disclosed above may be used for a recoating step.

After the cell modifying surfaces are replaced or recoated, the cells are reintroduced from the buffer container into the centrifugation chamber and the next modification step under centrifugation conditions can be performed.

In a further example for a sequence of processing steps during the process of the invention, the cell modifying surface may first be coated e.g. with BD Primaria™ to enhance the proliferation of the cells and then with virus particles for one or more transduction steps. The cell modifying surface may be recoated with new (same or different) virus particles between two transduction processes. For functionalizing the cell modifying surface with virus particles, the cells are rinsed from the surfaces and stored in a buffer container. After the coating process, the cells are reintroduced into the centrifugation chamber and the second culturing step can be started.

Batch and Continuous Modification

The centrifugation chamber and the method of the invention permit both the batch-wise and the continuous modification of cells. In a batch-wise modification, the cells either stay during the whole process within the chamber or are completely removed and after an intermediate step reintroduced into the chamber. Batch processing involves usually an intermediate storage of cells in a buffer container.

Continuous modification means that the cells are continuously introduced into and removed from the chamber during the modification process. Continuous modification involves e.g. a conical shaped centrifugation chamber or cell modifying surfaces and/or a flow of media through the chamber which transports cells as required. For continuous modification, the centrifugation chamber comprises at least two inlet/outlet ports for liquids and gases and optionally an intermediate storage of cells in a buffer container.

Introducing the cells in the chamber, rinsing cells into a buffer container, washing and coating of the cell modifying surfaces and reintroducing the cells into the chamber can be performed with the aid of pumps and tubes and controlled e.g. by appropriate software.

Supply of Nutrients and Overall Conditions

Temperature and gas composition of the centrifugation chamber can be controlled and adjusted if appropriate for the cell types or the modification steps to be performed. For this purpose, a heating and/or cooling means can be attached to the device of the invention.

In the method of the invention, it is preferred to cover the cells to be modified with a layer of liquid (media) as thin as possible to supply the cells with gases such as $O_2$, $N_2$ and $CO_2$ by diffusion. The thinner the film, the easier diffusion of gases and the better cells can be supplied. Therefore in another variant of the invention, the cell culturing liquid is moved over or relative to the cells e.g. by changes of the rotational speed or by adding additional media through the ports. Preferable, the liquid media is moved over the cells during rotation of the chamber in form of a liquid film with a thickness of less than 50 µm, less than 100 µm, less than 200 µm, less than 500 µm, less than 1000 µm or less than 2000 µm Films of cell culturing liquids having such thickness are sufficient to cover and supply the cells with the necessary nutrients and gases. The cells may be supplied with cell culturing liquids by constant movement of the liquid relative to the cells.

In another variant of the invention, the cell culturing liquids are exchanged or renewed during the modification process in a constant flow. For this variant, the device of the invention has at least two ports for inlet/outlet of cell culturing liquid. The exchange of liquids can be performed without stopping the rotation of the centrifugation chamber.

The cell culturing liquid (media) supplied to the cells may have the same composition during the entire modification process. It is furthermore possible to change the composition of the media during the modification process, for example by withdrawing a first medium and supplying a second medium from/to the chamber or by a constant flow of medium with a constant change of composition.

Cells to be Modified

The eukaryotic cells modified in the device and/or the method according to the invention may origin from any mammalian or human source, such as tumor, blood, tissue, bone marrow or cell lines, for example one or more cell types selected from the group consisting of human cells, fibroblasts, embryonic stem cells, keratinocytes, melanocytes, mesenchymal stem cells, epithelial cells, T-cells, regulatory T-cells, B-cells, NK-cells, neuronal cells, dendritic cells, stem cells (adult, embryonic, hemapoietic), cells originating from epithelium, ectoderm, endoderm, endothelium, mesoderm, epithelial tissue, basal lamina, vasculature, Connective tissue, fibrous tissues, Muscle tissue, visceral or smooth muscle, skeletal muscle, cardiac muscle, nervous tissue, brain, spinal cord, cranial nerves, spinal nerves or motor neurons.

The method and the device of the invention are especially suitable for modification of eucaryotic cells, preferable for modification of one or more cell types selected from the group of human blood and immune system cells consisting of Megakaryocyte (platelet precursor), Monocyte, Connective tissue macrophage (various types), Epidermal Langerhans cell, Osteoclast (in bone), Dendritic cell; lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), and tissue or tumor stem cells.

According to method of the invention at least two different cell types or cells of at least two different phenotypes can be modified.

The cells exhibit a different phenotype after modification. It is a further object of the invention to provide a cell composition modified by the method of the invention. Yet another object of the invention is to provide a cell composition with at least two layers, the layers comprising modified cells of different cell types or cells of a different phenotype.

Modification Techniques

It is an advantage of the cell culturing device and method according to the invention that the cells are pressed against the cell modifying surfaces by the centrifugal forces, thereby enlarging the cell surface adjacent to the functionalized cell modifying surfaces. Enlarging the cell surface enhances the chances of contact between for example a target cell to be modified and a feeder cell or a retrovirus.

Furthermore, the centrifugal forces bring the functionalized cultural surfaces in close contact with the membrane of the cells to be modified. The close contact causes the cell to act for example by signal transduction or uptake of the extracellular material into the cell. Modification techniques during the method of the invention may comprise genetic or cellular modification of the cells or the preparation of cellular layers.

Genetic Modification

The term "genetic modification of cells" refers to all processes manipulating the genetic program of a cell on the level of DNA, RNA or translation of RNA into proteins by introduction of oligo- and/or polynucleotides into the genetic material of the cell. The transfected material may be only transiently expressed, e.g. in form of plasmids within the cell, or the transfected material may be stably expressed by integration of the genetic material into the genome of the cell. Genetic modification during the method of the invention comprises all techniques of molecular cloning and transformation to alter the structure and characteristics of the genes of a cell to be modified. This may include using recombinant nucleic acid (DNA or RNA) techniques to form new combinations of heritable genetic material followed by the incorporation of such material into the cell.

The process of the invention may comprise various methods of introducing foreign nucleic acids into a eukaryotic cell, which are known to the skilled artisan.

Such methods include applying physical treatment, like, for example, applying nanoparticles or magnetofection, using chemical materials like cyclodextrin or cationic polymers such as DEAE-dextran or polyethylenimine or using biological particles (viruses) that are used as carriers.

Genetic modification of cells within the method of the invention comprises furthermore the use of genetic modifying agents resulting in a genetic modification of the cell. Such genetic modifying agents are nucleic acids, e.g. DNA or RNA. The nucleic acid may be naked or in complexes with carrier molecules such as polymers, liposomes, or microparticles. The DNA may be in linear form (oligonucleotides, polynucleotides) or in circularized form (e.g. DNA-plasmids). The RNA may be any kind of RNA known to exist in the cell (e.g. mRNA, miRNA, siRNA, shRNA). The nucleic acid (DNA or RNA) may be derivatives of the naturally occurring nucleic acids or may be chemically modified. For example, modified nucleotides may include: linked nuclear acid (LNA), 2-0-Me nucleotides, 2'-O-methoxyethyl, and T fluoro. Backbone modifications include, for example, phosphorothioate and phosphate.

Another genetic modifying agent are viral-based gene delivery system which involves genetically engineered recombinant viruses, like, for example, Adenovirus, Adeno- Associated Virus, Retrovirus, Vaccinia virus and Lentivirus, which carry the gene of interest in their capsid.

Genetic modifying agent also comprises chemical mutagens such as base analogues (e.g. 5-bromouracil (5-BU)) which are incorporated into DNA, agents modifying purines and pyridines or agents labilizing bases (e.g. nitrous oxide, hydroxylamine and alkylating agents) and agents producing distortions in DNA (e.g. fluorescent acridine dyes such as proflavine and acridine orange.

Genetic modification of cells within the method of the invention comprises for example introducing the nucleic acids, e.g. DNA or RNA, into the cell by using the already disclosed particles. The nucleic acid to be introduced into the cell may be covalently or non-covalently attached to the surface of the particles resulting in nucleic acid particle complexes. The nucleic acid particle complex may be immobilized on the cell modifying surface of the centrifugation chamber or the nucleic acid particle complexes may be given into the liquid/media within the centrifugation chamber. Then application of gravitational forces by rotation of the centrifugation chamber of the present invention drives the nucleic acid particle complexes towards and into the target cells, where the cargo is released.

Genetic modification of cells within the method of the invention comprises for example introducing the nucleic acids, e.g. DNA or RNA, into the cell using chemical-based transfection agents such as e.g. cyclodextrin, polymers, liposomes. The complexes of nucleic acid, e.g. DNA (linear or in circular form, e.g. plasmid) or RNA, and the chemical transfection agents, e.g. Lipofectamin® may be immobilized on the cell modifying surface of the centrifugation chamber. Then application of gravitational forces by rotation of the centrifugation chamber of the present invention drives the complexes of nucleic acid, e.g. DNA or RNA, and the chemical transfection agents towards and into the target cells. Alternatively, the complexes of nucleic acid, e.g. DNA or RNA, and the chemical transfection agents, e.g. Lipofectamin® may be given into the liquid/media within the centrifugation chamber resulting in transfection of the cell during the centrifugation of the centrifugation chamber.

Genetic modification of cells within the method of the invention comprises for example introducing the nucleic acids, e.g. DNA or RNA, into the cell using viral-based gene delivery systems (e.g. adenovirus, adeno-associated virus, retrovirus, and lentivirus). The virus or virus particles to be introduced into the cell may be covalently or non-covalently attached to the surface of the cell modifying surface of the centrifugation chamber or the virus or virus particles may be given into the liquid/media of the centrifugation chamber. Then application of gravitational forces by rotation of the centrifugation chamber of the present invention drives the virus or virus particles towards and into the target cells.

In some embodiments of the invention, cell modifying surfaces are optionally coated with affinity binding systems i.e. peptides enhancing retroviral transduction like for example, RetroNectin® (Takara, Japan). The multivalent nature of such affinity binding systems allows the simultaneous binding of cells and viruses, bringing the two into close physical proximity. The co-localization of viruses and cells facilitates infection, resulting in higher frequencies of stable gene transfer. Affinity binding systems may furthermore be coated on particles, which results in a co-localization of viruses and cells on the particles. The particles itself may be coated on the cell modification surface or may be utilized in suspension and immobilized on the cells by centrifugation.

In other embodiments of the invention the cell modifying surfaces are functionalized with modified, e.g. pseudotyped, viruses as vectors such as disclosed in WO2008/037458. Vectors derived from the gamma-retroviruses, for example, the murine leukemia virus (MLV), have become a standard tool for gene transfer technology and have been frequently used in clinical gene therapy trials (Ross et al., Hum. Gen Ther. 7:1781-1790, 1996). Pseudotyping of retroviral vectors, including HIV vectors or MLV vectors, refers to the incorporation of envelope proteins from heterologous viruses into the retroviral envelope membrane. Such pseudotyped retroviral vectors then exhibit a receptor phenotype similar to the virus from which the envelope protein was derived. Depending on the host range of said virus, the pseudotyped retroviral vectors will then have a broadened or a narrowed host range as compared to vector particles having the incorporated homologous retroviral envelope proteins. Useful pseudotyped vectors include MLV vectors pseudotyped with the HIV Env protein, the Ebola virus glycoprotein, or the baculovirus glycoprotein.

The measles virus (MeV), a prototype morbillivirus of the genus Paramyxoviridae, utilizes two envelope glycoproteins (the fusion protein (F) and the hemagglutinin protein (H)) to gain entry into the target cell. WO2008/037458 discloses the pseudotyping of retroviral vectors with heterologous envelope proteins derived from the Paramyxoviridae family, genus Morbillivirus. The incorporation of morbillivirus F and H proteins having truncated cytoplasmic tails into lentiviral vector particles allows an effective transduction of cells. In addition, these pseudotyped vector particles allow the targeted gene transfer into a given cell type of interest by modifying a mutated and truncated H protein with a single-chain antibody or ligand directed against a cell surface marker of the target cell, e.g. the stem cell marker CD133.

Cellular Modification

The term "modification of cells" refers to all processes which result in a morphological, functional, or molecular modification of the cells (e.g. activation, proliferation, reprogramming, dedifferentiation, differentiation or maturation). This embodiment of the invention comprises techniques like cell activation or stimulation for example by agonistic or antagonistic antibodies or cytokines or the in vitro modulation of cells like the in vitro expansion and/or genetic modification of lymphocytes. For example, T-lymphocytes can be cultured with antibodies against cell surface molecules like CD3 either bound to a macroscopic matrix like the cell modifying surfaces of the invention or in soluble form in the presence of antigen presenting cells, e.g. using peripheral blood mononuclear cells (PBMC) or fractions thereof as feeder cells and polyclonal stimuli. Instead of CD3 antibodies, specific antigens can be used for the stimulation and expansion of antigen-specific T-cell. In these types of cultures viral transductions of the T cells or any other type of genetic modification as described above can also be performed as already described, to achieve cellular modifications.

The cellular modification of cells within the method of the invention comprises for example the use of feeder cells or modifying cells that secrete certain metabolites, growth or differentiating factors into the medium or that directly deliver signals to the cells to be modified.

Feeder cultures, which secrete growth factors, can be prepared from splenocytes, macrophages, thymocytes, or fibroblasts. E.g. mouse embryonic fibroblasts (MEFs) are often used as feeder cells in human embryonic stem cell research. Genetically modified cells, such as K562 cells, stably transfected with stimulatory molecules, e.g. MHC class I or MHC class II, ligands for costimulatory molecules CD28, ICOS, Notch, CD137, CD40 or cytokines, e.g. IL-2 or IL-15 or facilitating molecules, e.g. Fc-gamma receptor (for labelling with Fc-bearing stimulatory molecules, e.g. antibodies or Fc-fusion proteins) can also be used.

The cellular modification with the method of the invention may further comprise the delivery of transcription factors (TFs) into cells promoting differentiation, transdifferentiation or dedifferentiation/reprogramming of the target cells. In this embodiment of the invention, the method comprises altering the state of a cell, for example an adult somatic cell, embryonic or adult stem cell, or a mesenchymal stem cell (MSC) by introducing one or more transcription factors or substances, which alter the expression or activity of said transcription factors, into the cells. The cells then alter the expression level of at least one polypeptide (e.g. Oct3/4 for an induced pluripotent stem cell) and/or epigenetic programming of the cell is changed.

Introducing the transcription factor into the target cells can be achieved by contacting a cell with a transcription factor, a polypeptide or fragment thereof fused to a protein transduction domain which allows entry of the protein into the cell or by any other means to transport active substances as defined above into cells and thereby altering the expression profile and/or epigenetic status, e.g. leading to reprogramming the cells. For example, Xie et al (2004, Cell: 117:663-676) disclose a method for the forced expression of a single TF to trigger a specialized B cell to transdifferentiate into a macrophage.

Cellular modification of cells during the methods of the invention can be further achieved with a cocktail of extrinsic signaling molecules to enhance differentiation and widen the spectrum of MSC plasticity. A suitable method to deliver TFs into MSCs is disclosed by Brazilay et al (2009), Stem Cells, 27:2509-2515.

The method of the invention is especially suited for the modification and expansion of T cells, either polyclonal or antigen-specific. The interaction of T-cells with a stimulatory agent like a stimulatory antibody or specific MHC/peptide complex on the surface of an antigen presenting cells (APC) can be increased by the increased gravitational force during centrifugation. For this purpose, the cultural surfaces can be coated with T cell stimulatory molecules like stimulatory antibodies against CD3, CD28 or CD137. It is advantageously to activate the T-cells to be modified with stimulatory antibodies in a soluble form or with particles coated with stimulatory antibodies during the process of the invention. Furthermore, T-cells can be co-cultured with APC, like T-cell depleted PBMC or artificial APC (e.g. K562 cells, transfected with Fc-gamma receptor and/or MHC molecules and/or costimulatory molecules, like CD137 ligand, or CD28 ligands), in various ratios (e.g.: 10:1 to 1:1000 T cells/APC).

Instead of stimulatory antibodies, T-cells can be co-cultured with specific antigens, e.g. defined antigenic peptides, purified defined proteins or protein mixtures or lysates of defined pathogens. This type of culture could be useful for activation or expansion of antigen-specific T-cells. Furthermore, any kind of T cell stimulatory agent can be used within the method of the invention, e.g. PMA, ionomycin, superantigens like SEB, lectins, like ConA or PHA.

The method of the invention allows the regulation of the interaction of T-cells with stimulating substances or cells via the centrifugation time and/or rotational speed. The interaction between the cells to be modified, the cultural surfaces and the substances or cells (like APC) applied to the centrifugation chamber can repeated as required to restimulate the cells or initiate their expansion. Furthermore, fresh media, cytokines other substances relevant for the cell modification/culture can be added in an automated fashion, without the necessity to interrupt the interaction between cells and coated surface or APC.

The above mentioned substances, ligands, factors, agents, particles or cells may be applied, coated or adhered to the cultural surfaces or introduced into the centrifugation chamber with the culturing liquids.

Cellular Layers

A layered cell composition according to the invention comprises at least two layers of cells with the same or different cell type or phenotype. Preferable, the layered cell composition comprises 2 to 10, especially 2 to 5 layers of cells with different cell type or phenotype. Each of these layers may comprise one or more (like 10 to 50) layers of the same cell type. Layered compositions of the invention may consist of complex cellular tissue, like stem cells on top of feeder cells, skin tissue or organs and may comprise same or different types of cells for example stem cells, fibroblasts, keratinocytes, melanocytes, epithelial cells, endothelial cells, antigen-presenting cells (B cells, dendritic cells, macrophages).

In this embodiment of the invention, for example cells of a first type are cultured on the cell modifying surface of the centrifugation chamber. On this first layer, cells of a second type are placed or immobilized by the centrifugal forces, which furthermore enhances the contact and interaction between the cells of the first and second type. Further layers or cell types can be placed on the existing cell layers resulting in a multilayer cell structure. In addition, matrices can be used for culturing the cells in three-dimensional structures. Such matrices are for example three-dimensional lattices e.g. proteoglycans, collagen or artificial matrices useful for culturing cells in three dimensions.

With the method and devices of the invention, it is possible to generate layered cell composition resembling human skin. Such layered cell compositions may be used, for example, as artificial skin.

Devices According to the Invention

A schematic view of a cell modification device according to the invention is shown in FIG. 1 with centrifugation chamber (a), rotational axis (g) and culturing surfaces (e). The culturing surfaces can be positioned parallel to the rotational axis (g), i.e. the normal vector of the culturing surfaces shares an angle of 90° with the rotational axis (g). By rotation of the chamber by axis (g), cells (f) are immobilized at the culturing surfaces (e) and can be supplied with cell culturing medium via at least one inlet/outlet port, like the shown inlet (c) and outlet port (d).

Devices of the invention may be equipped with one port which is used for both the introduction and removal of cells, media or gases into or out of the chamber. In another variant, at least two ports, for example one inlet and one outlet port for liquids and one or more ports for gas exchange are used. The ports are preferably integrated into the rotational axis of the centrifugation chamber and may in case of one inlet and one outlet port be attached from the same or from different sides of the centrifugation chamber.

Figure 2:
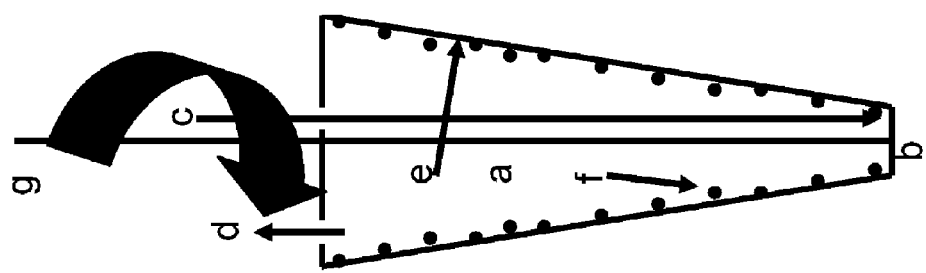
FIG. 2 shows an embodiment of the invention with a conical shaped chamber having culturing surfaces with a normal vector sharing an angle different than 90° (for example 105°) with the rotational axis (g).

A conical shaped chamber having culturing surfaces with a normal vector sharing an angle different than 90° (for example 105°) with the rotational axis (g) is shown in FIG. 2. In this embodiment, the cells and the media can move over the cell modifying surface depending on the rotational speed towards the side of the chamber having the wider diameter (in FIG. 2: upward). This can be advantageously used for genetic modification of the cells, for example with a cell modifying surface coated with virus particles for retroviral transduction. By movement of the cells over the surface, the contact area of the cells to the surface is enhanced, thereby enhancing the chance for cell modification like retroviral transduction. Furthermore, the cells are supplied by the movement of media over the cells in form of a thin film.

If the method of the invention comprises at a processing step wherein the cells are moving (or forced) over the cell modifying surface during rotation of the chamber, it is preferable to employ at least two different rotational speeds of the centrifugation chamber. For example in a first processing step, a higher rotational speed resulting in centrifugal forces of 100 g to 1000 g moves the cells towards the side of the chamber having the wider diameter and in a second processing step at lower rotational speed or even stopped chamber the cells slide down the cell modifying surfaces towards the base plate b). The processing steps of at least two different rotational speeds may be repeated as often as needed to achieve the desired level of cell modification.

Figure 3:
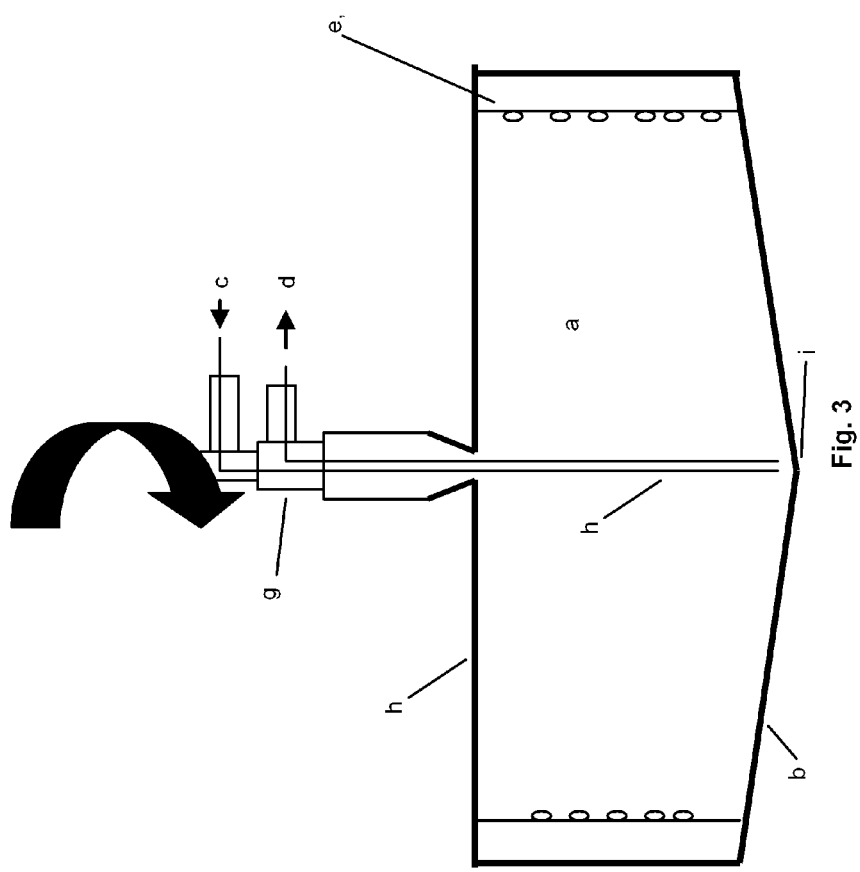
FIG. 3 shows another embodiment of the device of the invention, wherein the chamber and/or the element have a conical bottom or base plate (b) and at least one aperture or tube (h) reaching to the bottom of the chamber and/or the element.

FIG. 3 shows another embodiment of the device of the invention, wherein the chamber and/or the element have a conical bottom or base plate (b) and at least one aperture or tube (h) reaching to the bottom of the chamber and/or the element. During rotation, the cells (f) are immobilized at the cultural surfaces (e). If the rotation of the chamber is too slow or even stopped, the cells will accumulate at the lowest point (i) of the conical bottom or base plate (b) and can be removed by the internal tube (h) and outlet port (d).

The centrifugation chamber comprises at least one cell modifying surface at which the cells are immobilized by the rotation of the centrifugation chamber. The cell modifying surface is located in the centrifugation chamber or on the inner surface of the centrifugation chamber and may have any three dimensional shape like a wall or barrier as thin as mechanically possible with a height according to the sample size or the cell population to be modified.

The cell modifying surface may be located on the inner surface of the centrifugation chamber, a spiral-shaped element or on at least one cylindrical element. In one embodiment, the centrifugation chamber may have a base and cylindrical walls rotating about a rotational axis, with at least one cell modifying surface with a cell modifying substance disposed on the cylindrical walls, the cylindrical walls having a normal vector having an angle of 135–45° to the rotational axis. The centrifugation chamber may include at least one input/output port and the cells to be modified are immobilized at the cell modifying surfaces by the rotation of the centrifugation chamber at 2 to 2000 g. The input/output port may be integrated into the rotational axis of the centrifugation chamber. The cell modifying substance may be selected from the group of substances that enhance proliferation of cells, that induce genetic modification and that induce cellular modification of cells. The cell modifying substance may modify the behaviour, structure or function of cells.

The cell modifying surface may be located on at least one cylindrical element or structure like a wall or a layer. The number of cylindrical elements depends on the volume of the centrifugation chamber and/or the number of cells to be modified/cultured. In alternative, the cell modifying surface may be in shape of a spiral with or without an opening to the outside of the spiral to avoid the loss of medium due to centrifugal forces.

In another embodiment of the invention, the cell modifying surfaces are located on or are a part of an element insertable into the centrifugation chamber. Preferably, the cell modifying surfaces and/or the cylindrical element and the structures therein may comprise apertures or segments to facilitate the flow of medium to any part of the cell modifying surfaces in order to supply all cells immobilized on the cell modifying surface in sufficient manner. The cell modifying surfaces, the cylindrical element or the internal structures may furthermore comprise an appropriate number of spacer elements to ensure the mechanical stability of the cell modifying surfaces during centrifugation and to ensure the free flowing of cell culture liquid and gases through the chamber.

Cell modifying surfaces in form of a spiral can be obtained by winding up a film or foil to form a coil. Cell modifying surfaces located on a coiled film can be used without apertures or segments, since the liquid is forced through the chamber by the centrifugal forces. In another variant, the film comprises spacer elements to ease the flow of liquids between the film layers. The coil of film can be inserted in the chamber or into an appropriate concentric element to form a spiral. By using a film as substrate for the cell modifying surfaces, high surface areas for high cell densities or cell numbers can be provided.

Figure 4:
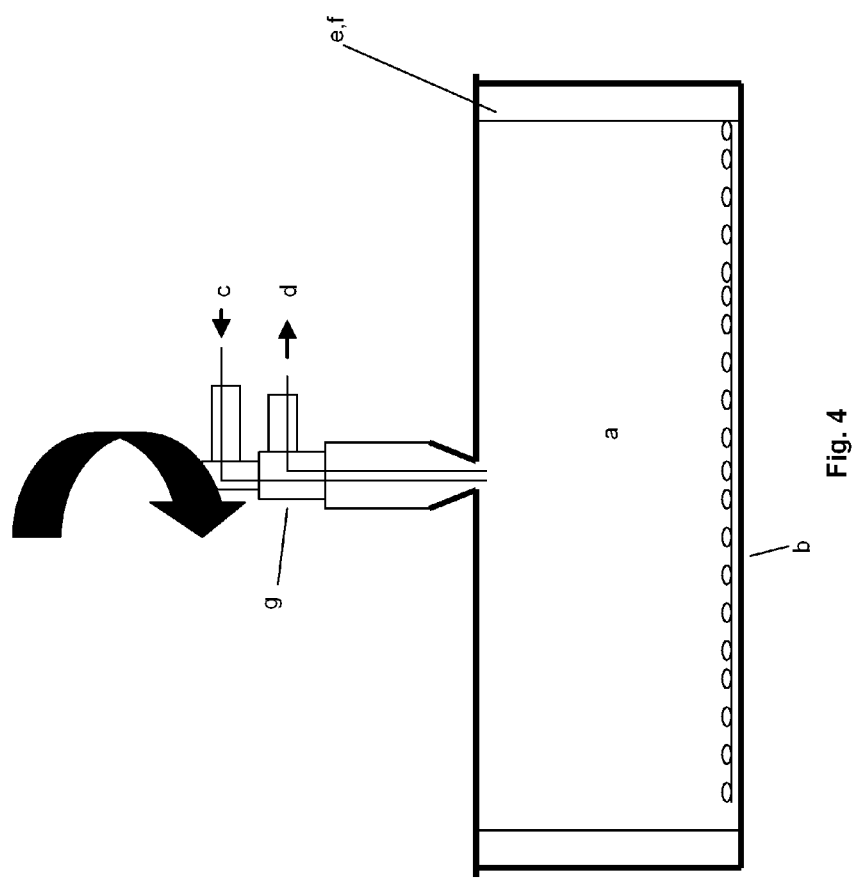
FIG. 4 shows several embodiments of centrifugation chambers with a plurality of internal structures or concentric elements in top view.

FIG. 4 shows several embodiments of centrifugation chambers with a plurality of internal structures or concentric elements in top view. Label (193) denominates the rotational axis and (194) the outer wall of the chamber. The cell modifying surfaces are labelled with (191) and (192) and may be concentric or spiral-shaped elements. The cell modifying surfaces can comprise spacer elements (195) generating sufficient space between the cell modifying surfaces for free flowing of cell culture liquid and gases.

It is furthermore possible that the centrifugation chamber comprises at least two cell modifying surfaces which are functionalized with the same or different at least one substance enhancing proliferation of cells, and/or inducing genetic modification and/or inducing cellular modification of cells. The cell modifying surfaces may have different functionality or different coated surfaces. In this embodiment, the device may comprise at least a first cell modifying surface with a normal vector having an angle of 135–45° to the rotational axis of the centrifugation chamber and at least a second cell modifying surface with a normal vector having an angle of (−45)–45° to the rotational axis of the centrifugation chamber.

Figure 5:
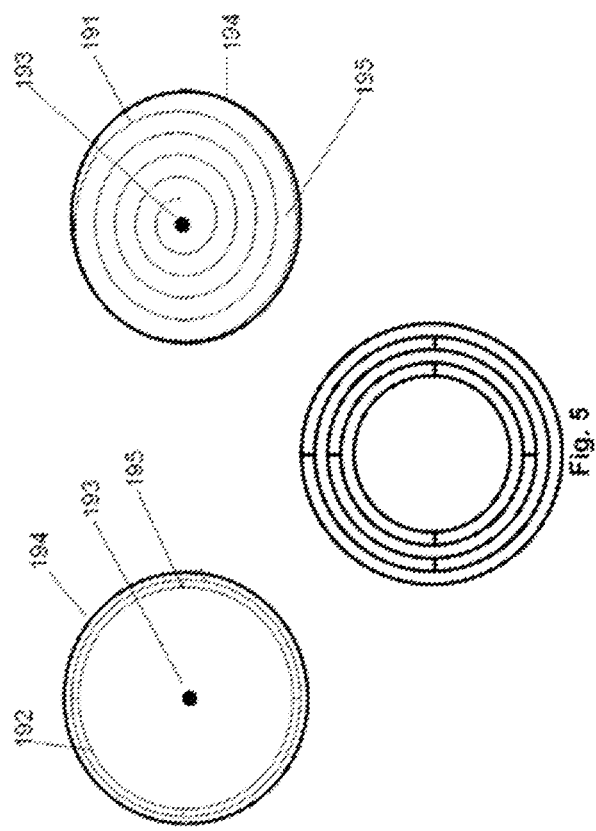
FIG. 5 shows an embodiment with two cell modifying surfaces; the first cell modifying surface (b) having a normal vector of about 90° to the rotational axis of the centrifugation chamber and the second cell modifying surface (e) having a normal vector of about 0° to the rotational axis of the centrifugation chamber.

For example, the cell modifying surfaces with a normal vector having an angle of 135–45° to the rotational axis of the centrifugation chamber can be functionalized for genetic modification of the cells, whereas the cell modifying surfaces with a normal vector having an angle of (−45)–45° to the rotational axis of the centrifugation chamber can be functionalized for proliferation of the cells. FIG. 5 shows this embodiment, with the first cell modifying surface (b) having a normal vector of about 90° to the rotational axis of the centrifugation chamber and the second cell modifying surface (e) having a normal vector of about 0° to the rotational axis of the centrifugation chamber. This embodiment of the invention allows at least two different modification steps at two different cell modifying surfaces in one chamber without the need to change the cell modifying surfaces during the process.

Figure 6:
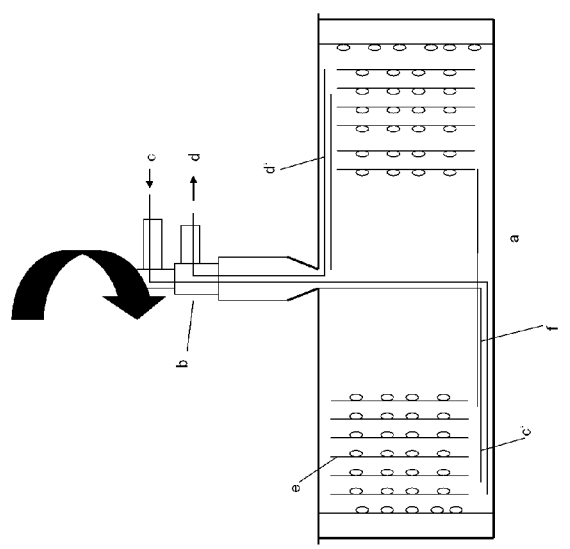
FIGS. 6 and 7 show a variant with concentric or spiral-shaped cell modifying surfaces (e) with a normal vector having an angle of 135-45° (shown 90°) to the rotational axis of the centrifugation chamber and a second cell modifying surface (f) with a normal vector having an angle of (−45)-45° (shown with an angle of 0°) to the rotational axis of the centrifugation chamber.
Figure 7:
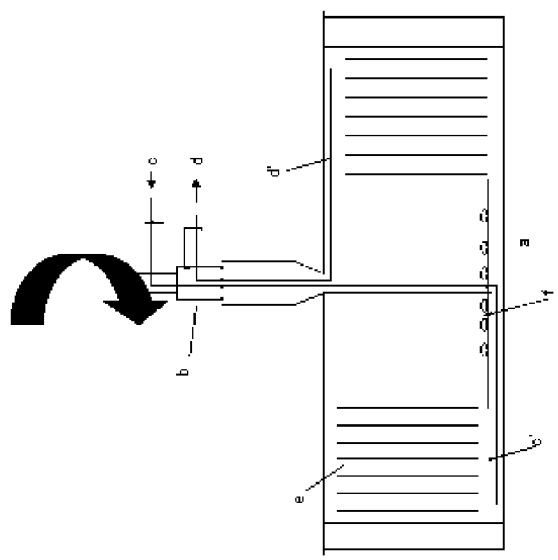

FIGS. 6 and 7 show another variant of this embodiment by way of example with concentric or spiral-shaped cell modifying surfaces (e) with a normal vector having an angle of 135–45° (shown 90°) to the rotational axis of the centrifugation chamber and a second cell modifying surface (f) with a normal vector having an angle of (−45)–45° (shown with an angle of 0°) to the rotational axis of the centrifugation chamber. The centrifugation chamber shown in FIG. 6 is in centrifugation state, where all cells are immobilized at the cell modifying surfaces (e) by the centrifugal forces. FIG. 7 shows the device after stopping the rotation of the chamber around axis b, the cells are rinsed from the cell modifying surfaces (e) and can be further cultured on the cell modifying surface (f) as shown in FIG. 7.

The cell culturing liquid may be supplied in a constant flow or is moved by variations of the speed of rotation over the cells. For example, in FIG. 8, the cell modifying surfaces (e) are not or not throughout connected to the second cell modifying surface f) and the top cover of the chamber, thereby allowing a flow of cell culturing liquid and gases via tubing or channels c' and d'. Optionally tubing or channel d' comprises apertures for distribution of the cell culturing liquid and gases over the cell modifying surfaces (e).

Figure 8:
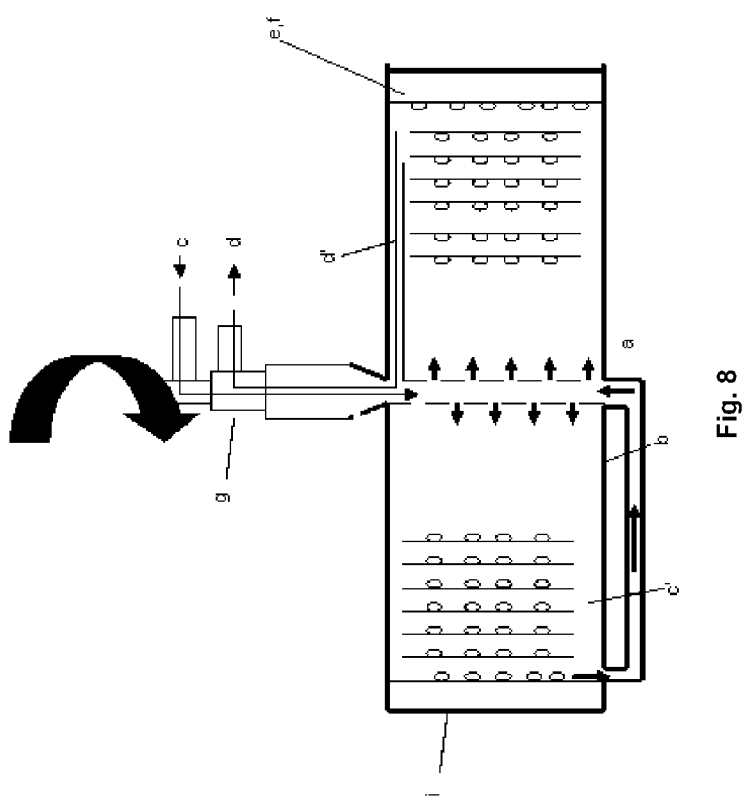
FIG. 8 shows an embodiment in which the cell modifying surfaces (e) are not or not throughout connected to the second cell modifying surface f) and the top cover of the chamber, thereby allowing a flow of cell culturing liquid and gases via tubing or channels c' and d'. Optionally tubing or channel d' comprises apertures for distribution of the cell culturing liquid and gases over the cell modifying surfaces (e).

The chamber may comprise at least one aperture allowing a flow of cell culturing liquid and/or gases into and out of the chamber. The aperture is preferable located in the axis (g) of the centrifugal chamber or concentric element as shown in FIG. 8. The cell culturing liquid and/or gases are supplied via inlet and outlet port c/d located in the rotational axis (g) and are then forced by the centrifugal movement over the cultural surfaces. The cell culturing liquids can be either withdrawn from the system via tubing or channel d' or directed back into the moulded element or the centrifugal chamber via bypass (c').

Figure 9:
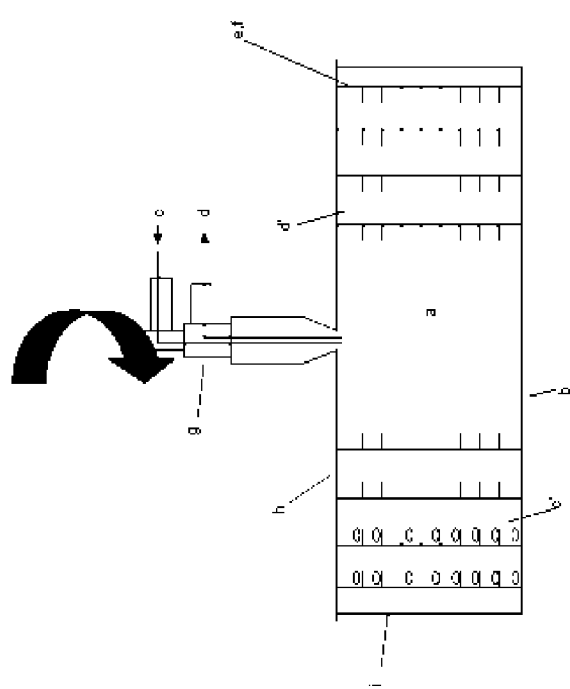
FIG. 9 shows an embodiment in which concentric or spiral-shaped cell modifying surfaces (f) with a normal vector having an angle of 135−45° (shown 90°) to the rotational axis of the centrifugation chamber and second cell modifying surface (h) with a normal vector having an angle of (−45)−45° (shown 0°) to the rotational axis of the centrifugation chamber are combined.

FIG. 9 shows another embodiment of the invention, in which concentric or spiral-shaped cell modifying surfaces (f) with a normal vector having an angle of 135–45° (shown 90°) to the rotational axis of the centrifugation chamber and second cell modifying surface (h) with a normal vector having an angle of (–45)–45° (shown 0°) to the rotational axis of the centrifugation chamber are combined. In this embodiment, the second cell modifying surfaces are attached to the first cultural surface (f) in a way that cells may be easily be transferred from the first to the second cultural surface and vice versa by change of rotational speed of the chamber. In this embodiment, the first and second cultural surfaces have a different functionalized coating thereby providing different modification to the cells.

The concentric elements as supporting structures for the cultural surfaces, the cultural surfaces itself and/or the centrifugation chamber may be made of various materials, preferably from plastics like, for example, polystyrene (PS), polyvinylchloride (PVC), polycarbonate, glass, poly acrylate, poly acrylamide, polymethylmethacrylate (PMMA), polyethylene terephthalate (PET), poly tetrafluorethylen (PTFE), thermoplastic polyurethane (TPU), silicone, poly ethylene (PE) poly propylene (PP), polyvinyl alcohol (PVA) or compositions comprising one or more of the above mentioned materials. In a preferred embodiment, the cell modifying surfaces may be coated with a biodegradable material, for example, collagen, chitin, alginate, and/or hyaluronic acid derivatives, poly lactic acid (PLA) polyglycolic acid (PGA) and their copolymers.

The size of the centrifugation chamber depends on the number of cells to be modified and may have the size of 2 cm to 50 cm in diameter and a height of 5 mm to 50 cm.

The centrifugation chamber of the device of the invention may be a single component with the cultural surfaces and/or supporting structures like concentric elements for the cultural surfaces. In another embodiment of the invention, the centrifugation chamber consists of an outer chamber (for example made from stainless steel) in which one or more concentric elements made from the above mentioned materials can be inserted. The cell modifying surfaces are then located on or are a part of the concentric elements.

The concentric elements may be disposable (i.e. single use) or may be designed and manufactured for re-use after washing and sterilization.

Furthermore, the cell modifying surfaces can be rough-textured, grooved and/or may comprise pockets or recesses to enhance the adherence of the cells to be cultured.

The process of the invention can be automated for example in a sample processing system as known from EP 0869838B1 and WO 2009/072003. The methods described here allow for automation in a closed cell modification device eliminating the risk of contamination of the cell culture compared to a standard non-closed transduction process, especially when the transduction process is repeated several-fold. In addition, safety of the operator is increased due to reduction of direct contact with biological hazardous material like retroviruses.

Systems According to the Invention

Yet another object of the invention are systems for cell modification, comprising:
a) a centrifugation chamber with at least one cell modifying surface with a normal vector having an angle of 135–45° to the rotational axis of the centrifugation chamber and at least one input/output port
b) a device to rotate the centrifugation chamber so as to apply a centrifugal force to cells The systems may furthermore comprise
c) at least one container containing the cells to be modified
d) at least one container for the cells to be modified
e) at least one container containing cell media
f) a tubing set connecting centrifugation chamber and container
g) at least one pump and
h) a plurality of valves The systems for cell modification can be operated by controlling the device to rotate the centrifugation chamber, the pump and the valves to introduce the cells to be modified and cell media into the centrifugation chamber, rotate the centrifugation chamber and remove modified cells from the centrifugation chamber.

Figure 10:
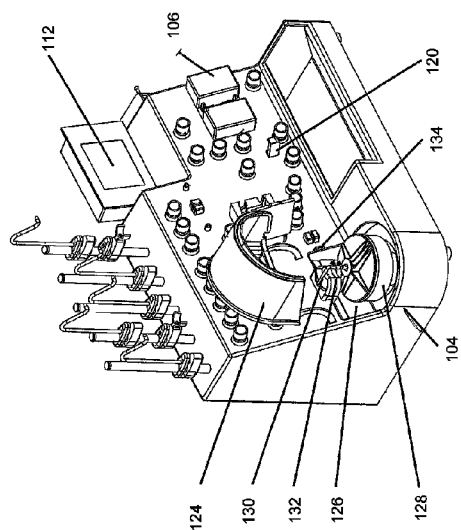
FIG. 10 is a system level drawing.

The system of the present invention can include various mechanical, electromechanical, and magnetic components. A system according to the invention is shown in FIG. 10, wherein the centrifugation chamber 128 having input/output port 130 can be connected to pump 108 and a plurality of valves 110. Container for the cells to be modified, the modified target cells and cell media are not shown but can be placed on hooks 114.

The system can optionally include a magnetic separation unit 106 with housing for positioning a separation column like a magnetic separation column.

The system 100 further includes a pump 108 and a plurality of fluid flow control means or valves, as illustrated by one or more valves 110. The components of the system 100 (e.g., centrifugation chamber, valves, pump, separation unit, etc.) can be coupled or connected by one or more flow paths so as to form a series of fluid pathways or fluid circuits. The system further includes a computer control system or unit 112 providing monitoring and/or control of one or more aspects of the system 100. The computer system 112, as described above, can include one or more input and/or output devices, graphical displays, user interfaces and may allow for manual and/or automated control of system 100 operation and functions. The computer control system 112 can include a module or system to process information (e.g., flow information, etc.) within the system 100 and can include a wide variety of proprietary and/or commercially available computers, components or electronics having one or more processing structures and the like, with such systems often comprising data processing hardware and/or software configured to implement any one or a combination of method steps as described herein. Software will typically comprise machine readable code of programming instructions embodied in a tangible media such as a memory, digital or optical recording media, optical, electrical, or wireless telemetry signals, or the like, and one or more of these structures may also be used to output or transmit data, signals, or information between components of the system in any of a wide variety of signal processing architectures.

The system can further include various supports, sensors, housings, etc. for various components that can be coupled with the present system to perform methods as described herein.

The system 100 further include one or more support structures 114 configured to hold and/or support various fluids, reagents, samples fluid reservoirs, filters, and the like that can be utilized with the system 100 according to the present invention. Support structures cart include various hook or hanger, or holder (e.g., filter holder or housing) configurations and are not limited to any particular design. Fluids, buffers, reagents, etc. positioned on a support 114 can be coupled to a fluid path or tubing, that can in turn be connected to more or more components of the system 100. The system 100 can include sensors for monitoring and/or further controlling fluid flow through the system. Sensors can include, for example, liquid sensors, which can include bubble detectors (ultrasonic detector), pressure sensors, and the like. Bubble detector 116 and pressure sensors 118 are shown. A support 120 is show, which can be configured to hold a filter or volume reduction unit. Collection area 122 can support collection containers, reagents, etc.

Processing unit 104 can include a housing or cover 124, that can be movable (e.g., removable) about one or more hinge. The cover 124 at least partially defines a processing area 126 that can be temperature controlled and coupled to temperature monitoring and control components that may be housed within the housing 105 of the system 100. The processing unit 104 includes a centrifugation chamber 128 configured for holding and processing (e.g., centrifugation, culturing, sample component separation, etc.) of a sample. The centrifugation chamber 128 shown is a rotating chamber held in position about an axis that can include an anti-rotation lock 130. The processing unit 104 can include one or more detection systems, such as an optical detector 132 positioned within the cover 124 and configured to detect or monitor processing of a sample in the chamber 128. One or more fluid input/output lines can be coupled to the chamber 128 and may be held in position by a holder 134.

All publications referred to herein are hereby incorporated by reference in their entirety.

EXAMPLES

The Examples described below are to exemplify the apparatus, methods, and systems of the invention and are not intended to limit the disclosure of the invention as described herein.

Example 1 Viral Transduction of T Cells with Disease-Specific T Cell Receptor Genes A use of the invention is the introduction of genes coding for a disease-specific T cell receptor into a polyclonal population of T cells, which may then be used for therapeutic injection into patients. The T cells are directed towards the target antigen, e.g. tumor cell or infected cells.

A centrifugation chamber providing cell modifying surfaces coated with RetroNectin® is supplied with a recombinant virus containing supernatant, wherein the virus encodes the target antigen, and rotated at surfaces by the gravitational forces generated by the rotation. Following this coating step, the chamber is rotated at low rotation speed and the T cells to be modified are introduced into the high rotational speed (e.g. 2000×g) for 2 hours. For improved viral transduction, the T cells are previously activated, e.g. by cultivation in the presence of antibodies against CD3 and CD28, either in the same centrifugation chamber or in a separate device. By centrifugation (e.g. 1000×g for 15 min) the T cells in the chamber come into intimate contact with the virus coated surface, allowing viral transduction. The centrifugation speed is adjusted to optimize the transduction. Transient lowering of the centrifugation speed allows detachment of the cells and subsequent centrifugation at high speed reattaches the cells at another point of the coated surface. This process can be repeated several times, e.g. to achieve multiple interactions of the cells with virus coated surfaces. Following this transduction process the rotation speed is stopped or reduced to a minimum, i.e. sufficient to keep the cells at the cultivation surface. During the process optimal cell culture media, containing appropriate amounts of nutrients and growth factors is added continuously to the chamber via the inlet port of the rotary chamber system. The centrifugation fixes the cells at a certain location, and therefore media can be added and removed without changing the location of the cell, i.e. without interfering with the modification process. The constant exchange of the medium without affecting the cell position, i.e. modification process, also allows to use a minimal medium volume at a given time, i.e. the distance of the cell attached to the culture surface to the gas reservoir/medium surface can be <5 mm. In this way optimal gas supply is guaranteed without the need for a steady state large medium volume, usually used as a reservoir of nutrients.

During the transduction process of high speed and/or lower speed, a steady flow of stimulation media over the cells or cell culture via the inlet and outlet port of the chamber is maintained. This removes transduction inhibitors and improves the target cell viability.

Each transduction process is adjusted to the optimal interaction of the cells with the virus particles (depending on cell and virus type) coated to the surface of the centrifugation chamber or moulded element by adaptation of the centrifugation speed (increasing or reducing the g number) leading efficient, fast, easy and safe handling of the transduction process.

Example 2. Activation and Expansion of Antigen-Specific T Cells

T cells can be activated and expanded by antigens loaded in or on antigen-presenting cells (APC). T cell activation requires intimate contact between the T cells and APC.

To improve T cell activation a system described herein is used to spin down APC and T cells in an appropriate ratio, e.g. 1:100 to 100:1. Either physiological cell mixtures such as PBMC, containing T cell and APC or defined cell preparations, e.g. purified T cells and APC, e.g. dendritic cells, B cells, macrophages, cell lines transfected with distinct MHC molecules, etc, mixed at an appropriate ratio are used. In addition antigens, proteins, peptides, cell lysates, and growth factors and/or co-stimulatory antibodies, e.g. anti CD28, antiCD137, may be added. The contact between the cells is rapidly induced and maintained at an appropriate level by centrifugation.

APC and T cells can be deposited in distinct layers, e.g. T cell on top of a layer of APC, enabling optimal contact of T cells to APC. In conventional culturing devices, cells slowly sediment in an uncontrolled fashion providing asynchronous and only suboptimal contact between APC and T cells. During cultivation centrifugation fixes the cells at a distinct position and therefore media, growth factors, co stimulatory molecules or antigens can be added in a controlled fashion without disturbing the cellular interaction. By changing the centrifugational speed the interaction between the cells is modulated at different phases of the culturing process, e.g. inducing firm contact at an early phase and reduced contact at later phases. This results in an accelerated and synchronous and more pronounced activation of T cells and in addition allows optimal control of the cellular microenvironment in terms of cellular composition, supply with nutrients, growth factors etc. Under these conditions the rapid and controlled activation of antigen-specific T cells is achieved.

The activated T cells are further purified, e.g. based on the expression of activation markers, such as cytokines, CD154 or CD137 by magnetic cell separation. Such cells can be generated against various antigens, e.g. pathogens, tumors or, in case of regulatory T cells against auto antigens. These cells can be used for cellular therapies.

A particular advantage of the invention is the fact, that the whole cell cultivation process including all described manipulations required to achieve optimal results can be performed in a closed system, i.e. with minimal risk of contaminations.

Example 3. Polyclonal Activation and Expansion of T Cells

The systems of the invention provide an optimized platform for polyclonal activation and expansion of T cells, comprising conventional T cells or regulatory T cells.

This example is similar to Example 2 except that instead of defined antigen, polyclonal stimuli are used, comprising antibodies against CD3 and co-stimulatory molecules, such as CD28 and/or CD137. These antibodies are added either in soluble form, requiring the addition of accessory cells bearing Fc-receptors, e.g. conventional antigen-presenting cells or cell lines transfected with Fc-receptors. Alternatively the added antibodies are immobilised on a macroscopic surface, e.g. a particle or bead ranging from about 30 nm to 100 µm. These immobilised antibodies are directly cultured with purified T cells, e.g. at ratios 1:4 to 4:1. As described above the system used allows regulated contact of T cells and stimulating agent and controlled addition of additional environmental factors, e.g. nutrients, cytokines, etc.

The polyclonal populations of T cells generated can be used in cellular therapies, e.g. polyclonal regulatory T cells for treatment of autoimmune or graft versus host disease or the prevention of organ transplantation.

The invention claimed is:

1. A cell modification device, comprising a centrifugation chamber having a base and cylindrical walls rotating about a rotational axis, wherein the cylindrical walls define cell modifying surfaces which are functionalized by coating the walls with a cell modifying substance the cylindrical walls having a normal vector having an angle of 135–45° to the rotational axis, wherein the centrifugation chamber comprises at least one input/output port integrated into the rotational axis and the cells to be modified are immobilized at the cell modifying surfaces by the rotation of the centrifugation chamber at 2 to 2000 g, wherein the cell modifying substance results in at least one of enhanced proliferation, induced genetic modification and induced cellular modification of cells.

2. The cell modification device according to claim 1, wherein the cell modifying substance is a substance that enhances proliferation of cells, and is selected from the group consisting of collagen types (I to VIII), fibronectin, gelatin, laminin, elastin, hyaluronic acid, keratan sulfate, chondroitin sulfate, heparin sulfate proteoglycans, poly-d-lysine, avidin, streptavidin, biotin, antibodies, antibodies against biotin or protein tags, protein tags like Ilsopeptag, BCCP, Myc-tag, Calmodulin-tag, FLAG-tag, HA-tag, His-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty tag, certia, poly lactate, polyvinyl alcohols, polysaccharides and dextran.

3. The cell modification device according to claim 1, wherein the cell modifying substance induces cellular modification of cells, and is selected from the group consisting of agonistic or antagonistic antibodies, cytokines, growth factors, (de-) activating ligands, pharmacologically active substances, mitogens, DNA or RNA-modifying substances.

4. The cell modification device according to claim 1, wherein the cell modifying substance induces a genetic modification of cells, and is selected from the group consisting of a virus, viral particle, adenovirus, retrovirus, lentivirus, RNA, DNA, non-coding small or large RNAs (i.e. siRNA, miRNA, shRNA), DNA, mRNA- or shRNA-expression plasmids, DNA, protein, ligand, receptor, cytokine, stimulating or deactivating antibody, pharmacological agent, feeder cells.

5. The cell modification device according to claim 1, wherein the cell modifying surface is located on the inner surface of the centrifugation chamber, a spiral-shaped element or on at least one cylindrical element, and wherein this cell modifying surface has a normal vector having an angle of 135–45° to the rotational axis.

6. The cell modification device according to claim 1, characterized in that the centrifugation chamber comprises at least two cell modifying surfaces which are functionalized with the same or different at least one substance enhancing proliferation of cells, and/or inducing genetic modification and/or inducing cellular modification of cells.

7. A method for modifying cells comprising the steps
introducing cells in a cell modification device, comprising
a centrifugation chamber having a base and cylindrical walls rotating about a rotational axis, with at least one cell modifying surface with cell modifying substance coated on the cylindrical walls, wherein the at least one cell modifying surface has a normal vector having an angle of 135–45° to the rotational axis of the centrifugation chamber wherein and comprising at least one input/output port,
immobilizing the cells on the cell modifying surfaces by the rotation of the centrifugation chamber at 2 to 2000 g
maintaining the rotation of the rotation of the centrifugation chamber until the cells are modified.

8. A method for modifying cells comprising the steps
introducing cells in a cell modification device, comprising
a centrifugation chamber having a base and cylindrical walls rotating about a rotational axis, with at least one cell modifying surface with cell modifying substance are coated on the cylindrical walls, wherein the at least one cell modifying surface has a normal vector having an angle of 135–45° to the rotational axis of the centrifugation chamber wherein and comprising at least one input/output port, immobilizing the cells on the cell modifying surfaces by the rotation of the centrifugation chamber at 2 to 2000 g maintaining the rotation of the rotation of the centrifugation chamber until the cells are modified, wherein the cells are modified by bringing into contact with at least one cell modifying surface which is functionalized with at least one cell modifying substance.

9. The method according to claim 8, wherein the cells are modified by immobilizing cells on at least one cell modifying surface and bringing into contact with particles being functionalized with at least one substance enhancing proliferation of cells, and/or inducing genetic modification and/or inducing cellular modification of cells.

10. The method according to claim 8, wherein the cells are subjected to at least two different gravitational forces by rotating the chamber with at least two rotational speeds.

11. A system for cell modification, comprising:
a centrifugation chamber having a base and cylindrical walls rotating about a rotational axis, with at least one cell modifying surface with cell modifying substance coated on the cylindrical walls, with at least one cell modifying surface with a normal vector having an angle of 135–45° to the rotational axis of the centrifugation chamber and at least one input/output port a device to rotate the centrifugation chamber so as to apply a centrifugal force to cells.

* * * * *